(12) United States Patent
Costello

(10) Patent No.: US 6,213,772 B1
(45) Date of Patent: Apr. 10, 2001

(54) ORAL ISOLATION DEVICE WITH EVACUATION CHAMBERS

(75) Inventor: William J. Costello, East Lansing, MI (US)

(73) Assignee: Drident, L.L.C., East Lansing, MI (US)

( * ) Notice: Subject to any disclaimer, the term of this patent is extended or adjusted under 35 U.S.C. 154(b) by 0 days.

(21) Appl. No.: 09/291,763

(22) Filed: Apr. 14, 1999

(51) Int. Cl.$^7$ .................................................. A61C 17/06
(52) U.S. Cl. .............................................. 433/93; 433/140
(58) Field of Search .................................. 433/93, 91, 94, 433/140, 136; 600/206, 238

(56) References Cited

U.S. PATENT DOCUMENTS

| | | | |
|---|---|---|---|
| 590,460 | * 9/1897 | Mehlig | 600/242 |
| 1,042,133 | 10/1912 | Marshall | 433/93 |
| 1,401,646 | 12/1921 | Ronn | 433/93 |
| 2,830,371 | 4/1958 | Dahl | 32/33 |
| 3,090,122 | 5/1963 | Erickson | 32/33 |
| 3,768,477 | 10/1973 | Anders et al. | 128/276 |
| 4,053,984 | 10/1977 | Moss | 32/33 |
| 4,215,984 | * 8/1980 | Reichley | 433/93 |
| 4,259,067 | 3/1981 | Nelson | 433/93 |
| 4,260,378 | 4/1981 | O'Neil | 433/93 |
| 4,632,093 | 12/1986 | Giorni | 128/12 |
| 4,992,046 | 2/1991 | Sharp | 433/93 |
| 5,037,298 | 8/1991 | Hickham | 433/93 |
| 5,232,362 | 8/1993 | Kanas | 433/93 |
| 5,460,524 | 10/1995 | Anderson | 433/93 |

* cited by examiner

Primary Examiner—John J. Wilson
Assistant Examiner—Melba Bumgarner
(74) Attorney, Agent, or Firm—Knechtel, Demeur & Samlan

(57) ABSTRACT

An essentially a U-shaped oral isolation device having a tongue arm, a buccal arm, and a hinge section is provided. The device is an essentially hollow member having an upper suction chamber and a lower suction chamber within the hollows of the oral isolation device. Each chamber further comprising suction inlet apertures through which saliva, fluid, aerosol mist, and debris can be evacuated from the operative site, and a suction outlet chamber through which the collected saliva, fluid, and debris are removed from the device. A U-shaped hinge member joins the buccal arm and the tongue arm. It has position memory which permits the user to squeeze the arm members toward one another for placement in the mouth and upon release, the arm members exert opposing positional influence against the tongue and cheek. Also provided is a method of use for the device in which the tongue arm and buccal arms are forced toward one another. The hinged member is then inserted into the patient's oral cavity and placed around the rearmost tooth. Upon proper placement of the device, the user releases the pressure on the arms of the device, the arms thereby exerting opposing positional influence against the cheek and tongue, resulting in retraction of the tongue and cheek, thereby creating a clear operative field. A reduced pressure high volume device is then attached to the upper chamber suction outlet and a low pressure reduced volume device is attached to the lower chamber outlet.

20 Claims, 3 Drawing Sheets

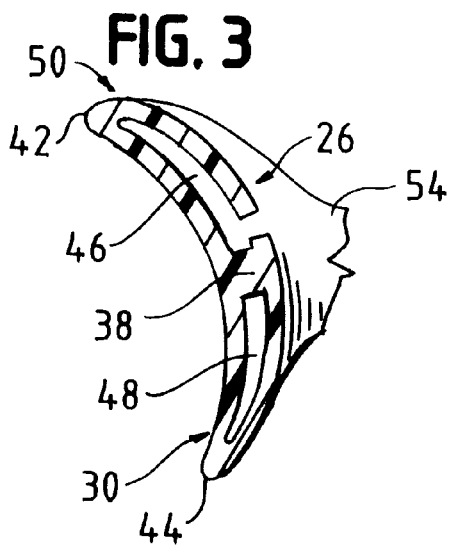
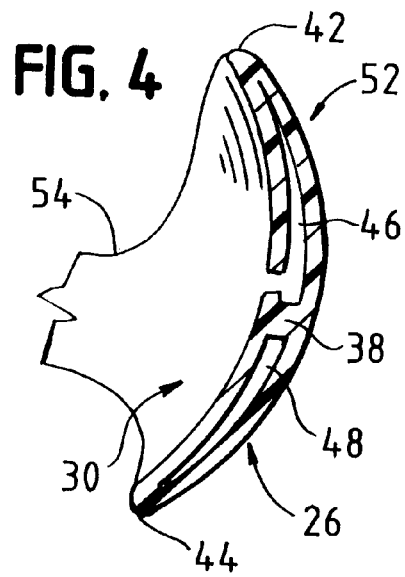
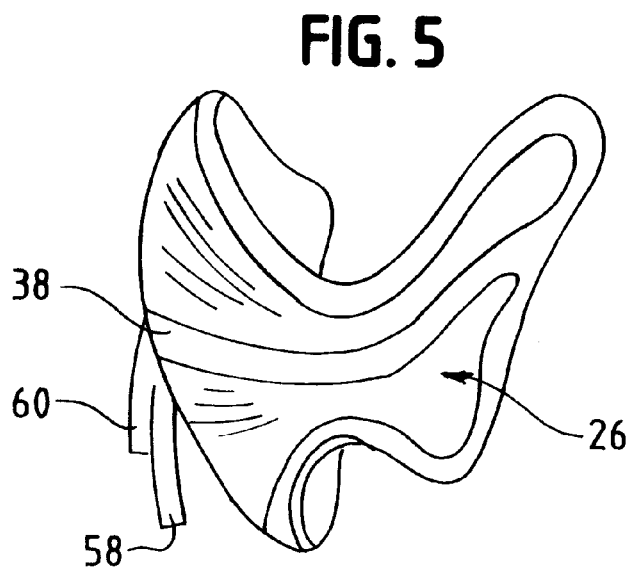

ORAL ISOLATION DEVICE WITH EVACUATION CHAMBERS

I. TECHNICAL FIELD

The present invention relates to oral isolation devices for use in dental procedures and, more particularly, to an oral isolation device which optimizes the size of the operating field, provides unobstructed cheek and tongue retraction, and further includes fluid, aerosol, and debris evacuation chambers adapted to attach to suction devices, thereby keeping the operative field dry without causing tissue damage to surrounding tissue.

II. BACKGROUND OF THE INVENTION AND PRIOR ART

During oral procedures, the dentist encounters many unique surgical difficulties. For instance, the oral cavity is a small space within which to work; it is bacteria laden and rich in blood supply; there is saliva, debris and applied fluid and aerosol buildup; and, finally, many patients have difficulty in keeping their tongues from entering the operative field.

Over the years, many appliances have been devised to assist in maintaining a clear and clean operative field. One example is seen in U.S. Pat. No. 1,042,133 to Marshall. This patent discloses a device for working on a patient's lower front teeth. This device includes a saliva ejector and a lower lip deflector and consists of a hollow double-bow tube having an exterior portion and an interior portion. The interior portion passes over the lower front teeth and rests below the tongue. The exterior portion has a lower lip deflector which hooks over the patient's lower lip exposing the front lower teeth. While this device is suitable for working on the front lower teeth, it has no application for use with the upper teeth or on lower teeth other than the front teeth. An additional shortcoming of this device is that it only provides for evacuation of fluid collecting near the lingual mucosa at the base of the tongue.

Two more examples are seen in U.S. Pat. No. 1,401,646 to Roan (a saliva ejector for use in dental procedures involving the lower jaw; it consists of two perforated tubular portions, one of which is disposed on the lingual side of the alveolar ridge and the other on the buccal side of the alveolar ridge. Optionally included is a tongue deflection plate) and U.S. Pat. No. 2,830,371 to Dahl (a variation of a hollow tube saliva ejector system having a tongue holder; this device further including a chin plate). While these two devices offer certain advances, they are not without shortcomings. First, they are satisfactory for use only in lower jaw procedures. They have no application for upper jaw procedures. Second, while the devices offer some tongue retraction capabilities, they do so by tongue depression. Tongue depression can be quite uncomfortable for the patient and is only a marginally effective technique since a patient's tongue can slip from beneath the depressor. Third, both devices only provide for evacuation of pooled saliva and fluid, with Dahl doing so only on the buccal side of the gums. Finally, neither device permits retraction of the cheeks. Thus, the devices do not significantly increase the size of the operating field.

Another example is seen in U.S. Pat. No. 3,090,122 to Erickson which teaches a dental appliance that provides for the collection and drainage of liquid and debris, partial retraction of an adjacent cheek and depression of the tongue, and a bite support to maintain the device's position and the patient's mouth open. A shortcoming of this device is that it requires the patient bite down on the device to hold it into place. This can lead to patient discomfort and movement of the device. A further shortcoming of this device is the placement system may cause obstruction of the operative field. A further shortcoming of this device is that it only retracts a small portion of the tongue and provides essentially no retraction of the cheek, thereby only slightly increasing the operative field. A final shortcoming of this device is that it collects only collected fluid and debris.

A further example is seen in U.S. Pat. No. 4,053,984 to Moss. This patent teaches a mouth prop consisting of upper and lower U-shaped sections, the sections having apertures for extracting fluid and debris, cheek deflectors, a tongue depressor, and upper and lower lip deflectors. While this device is an improvement in the art field, it is not without its shortcomings.

A first shortcoming is that the device provides for tongue depression instead of retraction; the drawback of which is discussed above. A second shortcoming is that the device fits around the front of a patient's mouth, thereby creating a potential obstruction to the operating field. Another shortcoming of the device is that while providing for cheek retraction, it does so only passively, thus it only minimally increases the size of the operating field. A last but significant shortcoming of the device is that while providing for fluid and debris evacuation at not only the mandibular level but also the maxillary level, it does so at only one suction volume. Thus, there is no ability to adjust suction flow volumes to maintain the optimum flow for a given area.

Examples of other prior art are found in U.S. Pat. Nos. 4,259,067, 4,260,378, 4,632,093, 4,992,046, 5,037,298, 5,232,362, and 5,460,524.

While the prior art provides certain advances in isolating oral tissue and evacuating saliva from an operative field, the prior art suffers five general shortcomings. First, while increasing the size of the operative field somewhat, none of the prior art maximizes the size of the operative field. The prior art generally provides only discomfort causing tongue depression and, at best, minimal cheek retraction. Second, the prior art, in some fashion or another, obstructs the operative field in which a dentist must work. Third, the prior art is all designed to be fixed in shape. It forces the patient's mouth to conform to it as opposed to the device conforming to the patient's mouth. Fourth, the devices which provide for saliva evacuation generally do so only in a passive sense. The devices are designed to fit on either the lingual or buccal mucosa near the base of the alveolar ridge. These designs only enable the devices to extract saliva and debris which have, through gravitational flow, settled in the bottom of the mouth. This is often ineffective inasmuch as a comfortable operating angle requires that a patient's head be tilted somewhat backwards. Thus, the saliva and debris do not always congregate or collect in a position convenient for evacuation by the device.

Fifth, the prior art that does provide an evacuation means other than in the floor of the mouth, does so only at the same suction volume as that of the lower jaw saliva evacuation. This invariably leads to a situation in which the misting aerosol spray, which keeps drill bits and teeth cool and clears away debris, is not efficiently evacuated from the operating field. If the suction flow rate is increased sufficiently to remove the misting spray, the suction apparatus positioned near the base of the mouth will create a seal with surrounding tissue, resulting in tissue damage and preventing removal of collected saliva and debris. If, on the other hand, suction flow is decreased to a level in which accumulated fluid can be extracted, the suction flow rate is ineffective at evacuating misting aerosol spray.

There is need, therefore, for an oral isolation device which provides an optimal size to the operative field by retracting both the tongue and the cheek adjacent to preselected oral tissue, maintains a clear operative field by creating no obstructions, and enables efficient simultaneous evacuation of saliva, aerosol, and debris from the base of the mouth and from the oral cavity.

III. OBJECTS OF THE INVENTION

It is an object of the present invention to provide an oral isolation device which optimally retracts the tongue and adjacent cheek away from teeth and surrounding oral tissue on which work is to be performed.

It is a further object of the present invention to provide such an oral isolation device which has a spring action which enables the device to self-adjust to the patient's mouth.

It is a further object of the present invention to provide such an oral isolation device which minimizes operative field obstruction.

It is another object of the present invention to provide such an oral isolation device that is essentially hollow and contains chambers having a plurality of suction inlet apertures and a suction outlet aperture for each chamber, the suction outlet apertures being adapted to be removably affixed to suction devices, thereby permitting each chamber to be individually adjusted as to suction flow.

It is yet a further object of the present invention to provide such an oral isolation device which is easy to use, causes no or minimal patient discomfort, and relieves the dentist or dental assistant from the need to reposition suctioning devices during a dental procedure.

IV. SUMMARY OF THE INVENTION

The above objects of the invention are provided for in an improved oral isolation device. According to the invention, the oral isolation device is essentially a U-shaped member having a tongue arm, a buccal arm, and a hinge section. The device is an essentially hollow member preferably made of two complementary essentially U-shaped halves. In the preferred embodiment, when the complementary halves are joined, an upper suction chamber and a lower suction chamber are created within the hollows of the oral isolation device. Each chamber further comprising suction inlet apertures through which saliva, fluid, and debris can be evacuated from the operative site, and a suction outlet chamber through which the collected saliva, fluid, and debris are removed from the device.

The arms of the oral isolation device are preferably ovoid in shape, with one arm being disposed against the tongue, and the opposite arm being disposed against the buccal mucosa. The arm disposed against the tongue is concave with respect to the tongue, and the arm disposed against the buccal mucosa is convex with respect to the buccal mucosa. The two arms are sized such that they create a barrier to the tongue and cheek entering the operative field, and are of a height sufficient to prevent the patient's mouth from closing.

A U-shaped hinge member joins the buccal arm and the tongue arm. The hinge member is smaller in height than the arm members. It has position memory which permits the user to pinch the arm members toward one another for placement in the mouth and upon release, the arm members directional induce the tongue and cheek away from the operative field.

Also provided is a method of use for the device in which the tongue arm and buccal arms are forced toward one another. The hinged member is then inserted into the patient's oral cavity and placed around the rearmost tooth, and preferably, posterior to the alveolar ridge, of that side of the mouth on which work is to be performed. Upon proper placement of the device, the user releases the pressure on the arms of the device, the arms thereby exerting retraction pressure to the cheek and tongue, resulting in retraction of the tongue and cheek, thereby creating a clear operative field.

A reduced pressure high volume device is then attached to the upper chamber suction outlet and a low pressure reduced volume device is attached to the lower chamber outlet.

In an alternative embodiment, the device is a solid member containing no chambers and is used for cheek and tongue retraction during dental procedures wherein saliva and debris evacuation is not required.

V. BRIEF DESCRIPTION OF THE DRAWINGS

FIG. 3 depicts a cross section view of the tongue retraction arm of the device.

FIG. 4 depicts a cross section of the cheek retraction arm of the device.

FIG. 5 depicts a lateral perspective view of the anterior of the device.

VI. DESCRIPTION OF THE PREFERRED EMBODIMENT

The following description of the preferred embodiment will be better understood with reference to the appended drawings. As those skilled in the art understand, the oral cavity is a difficult area within which to perform procedures. The dentist and patient are best served when the size of the operative field is optimized. The primary goal is to isolate the area in which a procedure is to be performed. A secondary goal is to keep that area as free as possible from collected saliva, fluid, aerosol, and debris. The present invention addresses those problems and concerns in an improved Oral Isolation Device (device) 20.

Figure 1:
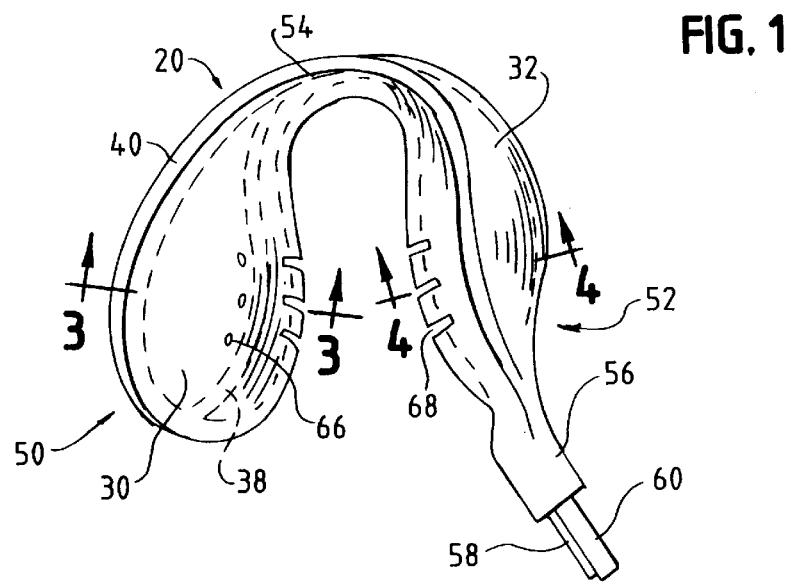
FIG. 1 depicts an top view of the inventive device.
Figure 2:
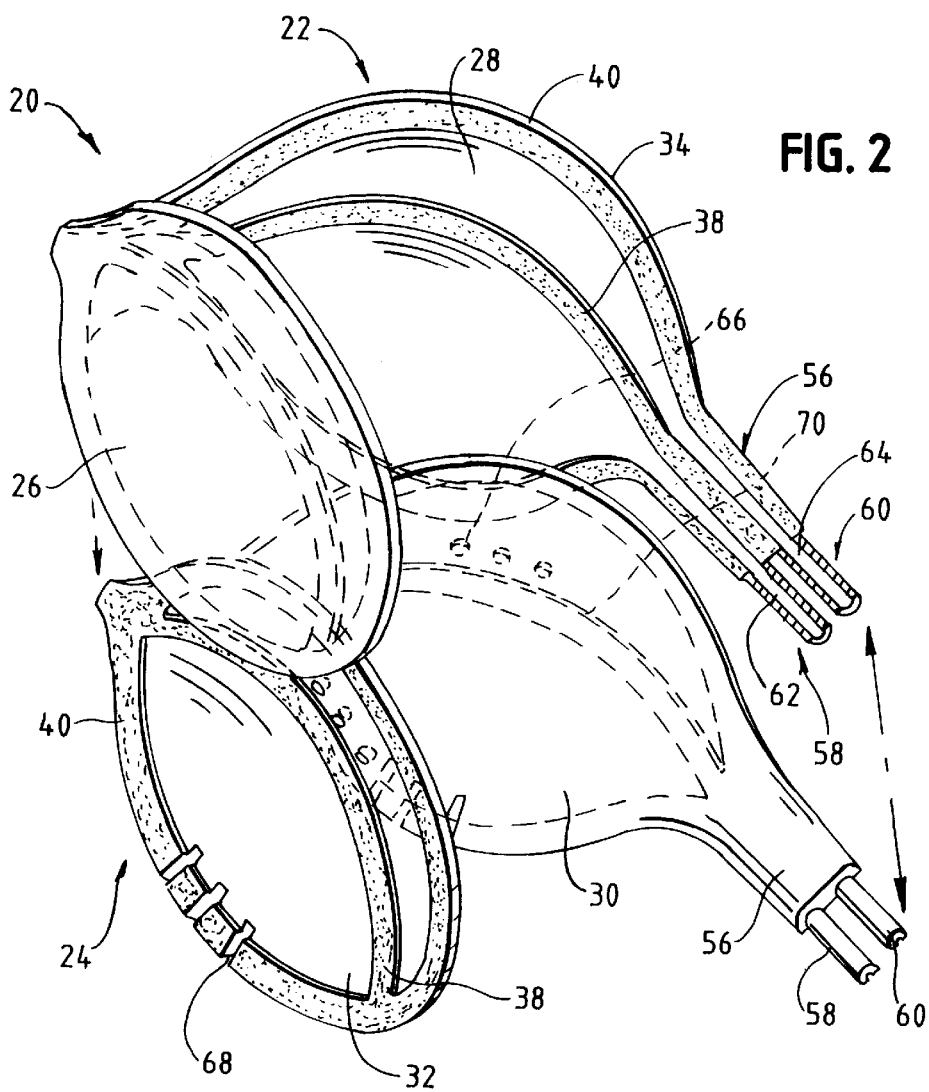
FIG. 2 depicts an exploded version of the device illustrating the two major sections which comprise the device as viewed from the side.

Turning to FIG. 1, a top view of device 20 is depicted. Turning to FIG. 2, it can be seen that in its preferred embodiment, device 20 is comprised of two sections, outer section 22 and inner section 24. While the preferred embodiment envisions an outer section and an inner section, this is done for manufacturing purposes only. The scope and spirit of the inventive device can be fullly realized through other means such as, but not limited to, an upper half and a lower half Outer section 22 further comprises outer wall 26 and inner side 28. Inner section 24 further comprises inner wall 30 and outer side 32. The perimeter 34 of outer section 22 curves slightly toward inner side 28 while the perimeter 34 of inner section 24 curves toward outer side 32. Thus, when outer section 22 and inner section 24 are coformed together, they form a hollow space within inner side 28 and outer side 32. Turning to FIG. 1, it can be seen that divider 38 extends along the horizontal length of device 20. As depicted in FIG. 2, divider 38 is shown positioned on inner side 28 of outer section 22. While divider 38 is shown in such a position for explanatory purposes, it is to be understood that divider 38 could be located also on outer side 32. Also, while divider 38 is shown in the drawings as essentially a uniform line, it is to be further understood that divider 38 may also be wider, creating a smaller space between divider 38 and edge 40. Divider 38 may also be formed into device 20 after outer section 22 and inner section 24 are coformed together.

During the manufacturing process, outer section 22 and inner section 24 may be coformed together through any conventional means such as ultrasonic welding. Other molding means such as thermal forming can also be used to manufacture the device. However, due to the complexity of creating an essentially hollow U-shaped device, the inventor found that welding two complementary sections to one another is preferred. Device 20 is preferably made of a semi-rigid material; plastic is ideal.

Turning to FIG. 3, it can be seen that once outer section 22 and inner section 24 are coformed together, an upper seam 42 and lower seam 44 create edge 40 (FIG. 1). As also seen in FIGS. 3 and 4, divider 38 defines an upper chamber 46 and a lower chamber 48. Thus, three dimensional space is created: a vertical space extending from lower seam 44 and upper seam 42, a front-to-back created by the U-shaped configuration of device 20, and a horizontal space created within the side wall. Thus, a hollow space defining the chambers is created.

Returning to FIG. 1, the completed apparatus can be broken down into essentially three sections; a tongue retraction arm 50, a cheek retraction arm 52, and a hinge member 54. As can be seen in FIG. 2, tongue retraction arm 50 and cheek retraction arm 52 are essentially ovoid in shape. Cheek retraction arm 52 further includes suction outlet member 56. At its free end, suction outlet member 56 further divides into low volume suction arm 58 and high volume suction arm 60. As seen in FIG. 2, low volume suction arm 58 and high volume suction arm 60 continue at separate passageways 62, 64 through the interior of suction outlet member 56. Low volume suction arm 58 terminates in lower chamber 48 (FIGS. 3 and 4) and high volume suction arm 60 terminates in upper chamber 46 (FIGS. 3 and 4).

As seen in FIG. 1, a posterior view of device 20, tongue retention arm 50 is concave with respect to the tongue and as seen in FIGS. 3 and 4, cheek retraction arm 52 is convex with respect to the cheek. The inventor found that these geometric configurations optimize the retraction ability of tongue retractor arm 50 in retracting the tongue and cheek retraction arm 52 in retracting the cheek to create an optimum sized operating field while at the same time creating a comfortable fit for the patient.

Tongue retraction arm 50 and cheek retraction arm 52 are preferably ovoid in shape. This shape also adds to the retraction and comfort attributes of device 20. It is also preferable that tongue retraction arm 50 and cheek retraction arm 52 are of such a vertical size as to encourage a patient to keep his mouth open during a dental procedure.

As described above, in the preferred embodiment, device 20 is manufactured as a two piece device. For purposes of the preferred embodiment, however, the device is broken down into the tongue retraction arm 50, cheek retraction arm 52, and hinge 54. It is to be understood that while hinge 54 is described as a separate section of the device and can be viewed as a separate section in use of the device, in the preferred embodiment, hinge 54 is part and parcel of the overall apparatus. As can be seen in FIGS. 1, 3, and 4, hinge 54 is of a height less than that of tongue retraction arm 50 and cheek retraction arm 52. This is beneficial in that it makes hinge 54 easier to position and more comfortable for the patient than if hinge 54 were the same height as the retraction arms. Hinge 54 has position memory, which is beneficial in placement of the device 20, as more fully described below. Upper chamber 46 and lower chamber 48 continue unobstructed through hinge 54 from cheek retraction arm 52 to tongue retraction arm 50.

As can be seen in FIGS. 1 and 2, inner section 24 also includes a plurality of ports 66 in upper chamber 46 and a plurality of slots 68 in lower chamber 48. While the drawings depict the plurality of ports 66 near the upper edge 70 of divider 38, the placement in this area is not critical. Likewise, the depiction of slot 68 near edge 40 of lower chamber 48 is not critical. As described more fully below in use of device 20, ports 66 should be positioned so that they create optimum suctioning power for the removal of aerosol mist and debris floating within the oral cavity during a dental procedure. Slots 68 should be positioned in an area of lower chamber 48 such that they are most effective in evacuating accumulated saliva, fluid, and debris from the lower portion of the jaw during a dental procedure.

As those skilled in the arts will quickly realize, however, port 66 should be placed along the plane of occlusion since this placement optimizes the area in which aerosol mist and floating debris are found and also is in the field of vision for a dentist during procedures.

Figure 6:
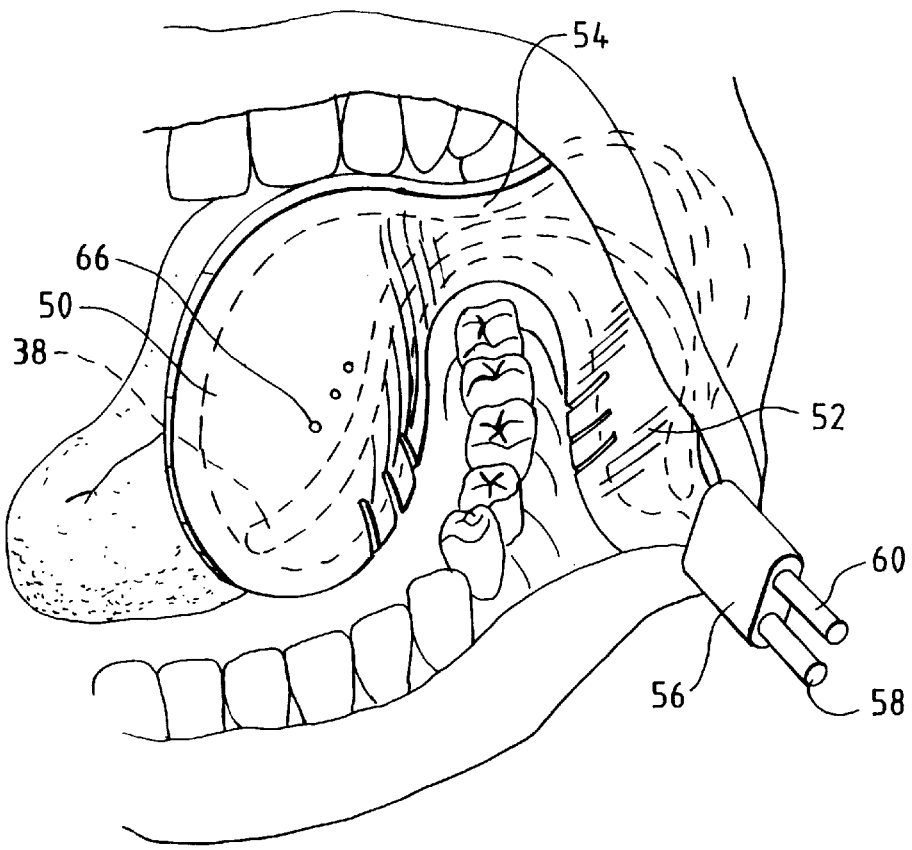
FIG. 6 illustrates placement of the inventive device in a patient's mouth.

To use device 20, the dentist or dental assistant grasps device 20 so that hinge 54 faces the posterior of the oral cavity and tongue retraction arm 50 and cheek retraction arm 52 face the anterior of the oral cavity. The dentist or dental assistant then applies compression pressure to tongue retraction arm 50 and cheek retraction arm 52, squeezing the two arms close to one another. Device 20 is then placed in a patient's mouth so that hinge 54 is inserted first and is fitted around the rear most teeth, and preferably around the posterior edge of the alveolar ridge. When in proper position, hinge 54 will be behind the rear most tooth, cheek retraction arm 52 will be on the buccal side of the alveolar ridge, and tongue retraction arm 50 will be on the lingual side of the alveolar ridge. Once device 20 is placed in proper anterior—posterior position, the dentist or dental assistant then releases the compression on tongue retraction arm 50 and cheek retraction arm 52. Upon release of the compression pressure, the position memory of hinge 54 causes the tongue retraction arm 50 and cheek retraction arm to move in opposing directions, the tongue retraction arm 50 thereby retracting the tongue and the cheek retraction arm 52 thereby retracting the adjacent cheek. Placement of device 20 can be visualized in FIG. 6. As also seen in FIG. 6, the only portion of device 20 that protrudes from the patient's mouth is suction outlet member 56 which extends in a downward position near the most lateral side of the patient's mouth.

High volume suction arm 60 is removably attached to a high volume suction apparatus and low volume suction arm 58 is removably attached to a low volume suction apparatus. In this manner, a high volume of suction can be applied to the upper chamber 46, thus resulting in effective removal of aerosol mist and debris free-floating in the oral cavity. At the same time, low volume of suction pressure can be applied to the lower chamber 48, thus effectively removing collected saliva, fluid, and debris from the lingual and buccal base of the mouth without causing damage to the surrounding mucosa.

Figure 7:
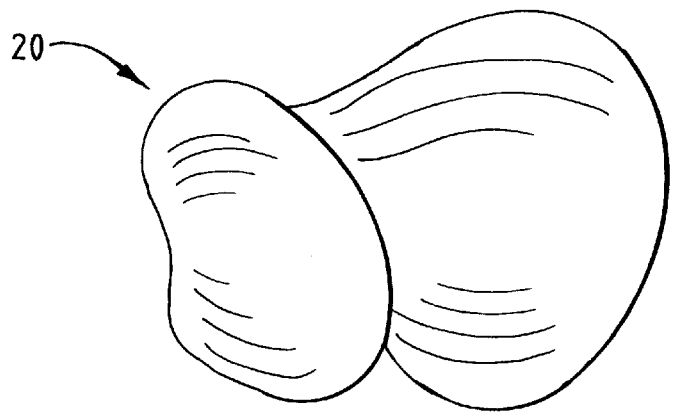
FIG. 7 depicts an alternate embodiment of the inventive device wherein the device is a solid member having no suction outlet arm.

In an alternate embodiment, as depicted in FIG. 7, the inventor contemplates use of the device without the necessity of attaching it to suction apparati. In such use, the device as described above can be used without attaching high volume suction arm 60 and low volume suction arm 58 to a suction apparatus. However, the inventor contemplates that the device can be made so that it is a solid or hollow member having no internal chambers, ports, slots or suction outlet member. In this alternative embodiment, device 20 is positioned in the same manner as describe above, with the only exception being that suction outlet member 56 will not be extending from the mouth and, obviously, no suction apparatus being applied to device 20.

The above description of the preferred embodiment is for illustration purposes only. As those skilled in the arts will quickly realize, there are many variations of the inventive device which are possible yet remain within the scope and spirit of the invention. Accordingly, the inventive device is only to be limited by the appended Claims.

What is claimed:

1. An oral isolation device for use in dental procedures comprising:
    an essentially U-shaped retraction member, the retraction member further being an essentially hollow member having an inner wall and an outer wall, and further including a divider within the hollow area, the divider defining an upper chamber and a lower chamber, the upper chamber having a first suction outlet for removably attaching to a suction device and a plurality of ports extending through the inner wall, the lower chamber having a second suction outlet for removably attaching to a suction device and a plurality of apertures extending through the inner wall.

2. The oral isolation device of claim 1 further including means for retracting a check.

3. The oral isolation device of claim 2 wherein the means for retracting the cheek is essentially oval in shape.

4. The oral isolation device of claim 2 wherein the means for retracting the cheek is convex in relation to the cheek.

5. The oral isolation device of claim 1 further including means to retract the tongue.

6. The oral isolation device of claim 5 wherein the means for retracting the tongue is generally oval in shape.

7. The oral isolation device of claim 5 wherein the means for retracting the tongue is generally concave with respect to the tongue.

8. An oral isolation device for use in dental procedures to isolate preselected oral tissue by retracting a cheek and tongue adjacent to the preselected oral tissue comprising an essentially U-shaped member having a cheek retraction portion, a tongue retraction portion, and a hinge member, the cheek retraction portion and tongue retraction portion being co-joined to each other by the hinge member the hinge member providing positional memory to enable the tongue retraction portion and the cheek retraction portion to be compressed toward one another for placement of the oral isolation device and then released causing the tongue retraction portion to retract the tongue from the teeth and the cheek retraction portion to retract the adjacent cheek from the teeth, the retraction of the tongue retraction portion and the cheek retraction portion providing an opening and preventing an obstruction to the isolated preselected oral tissue.

9. The oral isolation device of claim 8 further including means for retracting a cheek.

10. The oral isolation device of claim 9 wherein the means for retracting the cheek is essentially ovoid in shape.

11. The oral isolation device of claim 9 wherein the means for retracting the cheek is convex in relation to the cheek.

12. The oral isolation device of claim 8 further including means to retract the tongue.

13. The oral isolation device of claim 12 wherein the means for retracting the tongue is generally ovoid in shape.

14. The oral isolation device of claim 12 wherein the means for retracting the tongue is generally concave with respect to the tongue.

15. The oral isolation device of claim 8 wherein the hinge member is of a height less than the cheek retraction portion and the tongue retraction portion.

16. An oral isolation device for dental procedures which isolates preselected teeth by retracting a patient's tongue and cheek adjacent to the preselected teeth comprising:
    a first wall member for retracting the tongue;
    a second wall member for retracting the cheek;
    a substantially U-shaped center member connecting the first wall portion to the second wall portion, the essentially U-shaped center member having a memory which causes opposing lateral pressure on the first wall member and the second wall member;
    an upper vacuum chamber extending within the first wall member, second wall member, and U-shaped center member, the upper vacuum chamber further having an inner wall portion, an outer wall portion, and a free end, the inner wall portion further including a plurality of apertures and the free end further including a vacuum outlet member;
    a lower vacuum chamber extending within the first member, second wall member, and U-shaped center member, the lower vacuum chamber further including an inner portion, an outer portion, and a free end, the inner portion further containing a plurality of apertures and the free end containing a vacuum outlet member; and
    means for supplying a vacuum to the upper chamber and the lower vacuum chamber.

17. The apparatus according to claim 16 wherein the first wall member extends from the front of the mouth to the rear of the mouth and is substantially oval in shape along its vertical axis, the first wall member being concave with respect to the tongue.

18. The apparatus according to claim 16 wherein the second wall member extends from the front of the mouth to the rear of the mouth and is substantially oval in shape along its vertical axis, the second wall member being convex with respect to the cheek.

19. A method of creating a dental operating field comprising the steps of:
    exerting squeezing pressure upon an oral isolation device having a tongue retraction portion and a cheek retraction portion, the tongue retraction portion and cheek retraction portion each having a free end and a hinged end, the tongue retraction portion and cheek retraction portion hinged to one another at a hinge, thereby forming an essentially U-shaped device, so that the tongue retraction portion and cheek retraction portion move toward one another;
    inserting the oral isolation device into a patient's mouth in such a manner that the hinge is inserted into the patient's mouth before the free ends of the tongue retraction portion and cheek portion retraction;
    positioning the hinge around the posterior teeth on one side of the patient's mouth; and
    releasing the exertional force on the tongue retraction portion and the cheek retraction portion thereby retracting the tongue with the tongue retraction portion and the cheek with the cheek retraction portion.

20. A method of creating a dental operating field comprising the steps of:

exerting a squeezing closing force upon an oral isolation device having a tongue retraction portion and a cheek retraction portion, the tongue retraction portion and cheek retraction portion each having a free end and a hinged end, the tongue retraction portion and cheek retraction portion hinged to one another at a hinge, thereby forming an essentially U-shaped device, the oral isolation device further being characterized by being an essentially hollow member having an upper chamber and a lower chamber, the upper chamber further comprising a plurality of ports and a suction outlet member, and the lower chamber further comprising a plurality of apertures and a second suction outlet member;

inserting the oral isolation device into a patient's mouth in such a manner that the hinge is inserted into the patient's mouth before the free ends of the tongue retraction portion and cheek retraction portion;

positioning the hinge around the posterior teeth on one side of the patient's' mouth;

releasing the exertional force on the tongue retraction portion and the cheek retraction portion thereby retracting the tongue with the tongue retraction portion and the cheek with the cheek retraction portion; and, attaching the upper chamber suction outlet to a vacuum device and the lower chamber second suction outlet member to a second suction device.

* * * * *

UNITED STATES PATENT AND TRADEMARK OFFICE
CERTIFICATE OF CORRECTION

PATENT NO. : 6,213,772 B1
DATED : April 10, 2001
INVENTOR(S) : William J. Costello It is certified that error appears in the above-identified patent and that said Letters Patent is hereby corrected as shown below:

<u>Claim 2,</u>
Line 2, change "check" to -- cheek --

<u>Claim 8,</u>
Line 7, insert -- , -- after "member"

Signed and Sealed this

Second Day of October, 2001

Attest:

NICHOLAS P. GODICI
Attesting Officer
Acting Director of the United States Patent and Trademark Office